United States Patent
Hodorek et al.

(10) Patent No.: US 10,842,638 B2
(45) Date of Patent: Nov. 24, 2020

(54) IMPLANTS, SYSTEMS AND METHODS OF USING THE SAME

(71) Applicant: IGNITE ORTHOPEDICS LLC, Warsaw, IN (US)

(72) Inventors: Brian C. Hodorek, Winona Lake, IN (US); Matthew J. Purdy, Winona Lake, IN (US); Russ M. Parrott, Winona Lake, IN (US); J. Michael Wiater, Beverly Hills, MI (US); Anand M. Murthi, Baltimore, MD (US); Matthew J. Smith, Columbia, MO (US); Derek J. Cuff, Venice, FL (US); Andrew Jawa, Cambridge, MA (US); Luke Austin, Haddonfield, NJ (US)

(73) Assignee: IGNITE ORTHOPEDICS LLC, Warsaw, IN (US)

( * ) Notice: Subject to any disclaimer, the term of this patent is extended or adjusted under 35 U.S.C. 154(b) by 0 days.

(21) Appl. No.: 16/799,438

(22) Filed: Feb. 24, 2020

(65) Prior Publication Data
US 2020/0188124 A1 Jun. 18, 2020

Related U.S. Application Data

(63) Continuation of application No. PCT/US2019/043986, filed on Jul. 29, 2019.

(60) Provisional application No. 62/711,425, filed on Jul. 27, 2018.

(51) Int. Cl.
*A61F 2/40* (2006.01)
*A61F 2/30* (2006.01)

(52) U.S. Cl.
CPC ........ *A61F 2/4081* (2013.01); *A61F 2/30749* (2013.01); *A61F 2002/30205* (2013.01); *A61F 2002/30242* (2013.01); *A61F 2002/30383* (2013.01); *A61F 2002/30841* (2013.01)

(58) Field of Classification Search
CPC .... A61F 2/38; A61F 2/389; A61F 2/40; A61F 2/4081; A61F 2002/30331; A61F 2002/30841; A61F 2002/30884
See application file for complete search history.

(56) References Cited

U.S. PATENT DOCUMENTS

| | | |
|---|---|---|
| 4,725,280 A | 2/1988 | Laure |
| 5,928,285 A | 7/1999 | Bigliani |
| 6,364,910 B1 | 4/2002 | Shultz |

(Continued)

FOREIGN PATENT DOCUMENTS

| | | |
|---|---|---|
| DE | 69838625 T2 | 7/2008 |
| WO | 2008098061 | 8/2008 |

OTHER PUBLICATIONS

International Search Report and Written Opinion of the International Searching Authority for PCT/US2019/043986, dated Dec. 4, 2019, 13 pages.

*Primary Examiner* — Brian A Dukert
(74) *Attorney, Agent, or Firm* — Heslin Rothenberg Farley & Mesiti P.C.; Jacquelyn A. Graff, Esq.

(57) ABSTRACT

Implants, device, systems and methods for replacing an articulation surface in a joint, for example, a glenoid implant with an articular surface and an opposing bone contacting surface having a ring and post extending therefrom that respectively mechanically connect with cortical bone and cancellous bone of a glenoid. Methods for implanting the glenoid implant are also disclosed.

42 Claims, 8 Drawing Sheets

(56) References Cited

U.S. PATENT DOCUMENTS

| | | |
|---|---|---|
| 6,875,234 B2 | 4/2005 | Lipman |
| 6,911,047 B2 | 6/2005 | Rockwood, Jr. |
| 7,713,305 B2 | 5/2010 | Ek |
| 8,007,538 B2 | 8/2011 | Gunther |
| 8,425,614 B2 * | 4/2013 | Winslow ............... A61F 2/4003 623/19.11 |
| 8,778,028 B2 * | 7/2014 | Gunther ............. A61B 17/1659 623/19.11 |
| 9,381,086 B2 | 7/2016 | Ries |
| 9,545,311 B2 | 1/2017 | Courtney, Jr. |
| 9,956,083 B2 | 5/2018 | Humphrey |
| 9,962,266 B2 | 5/2018 | Humphrey |
| 10,433,969 B2 | 10/2019 | Humphrey |
| 2001/0037153 A1 | 11/2001 | Rockwood, Jr. |
| 2003/0055507 A1 | 3/2003 | McDevitt |
| 2005/0216090 A1 | 9/2005 | O'Driscoll |
| 2006/0195194 A1 | 8/2006 | Gunther |
| 2007/0225818 A1 | 9/2007 | Reubelt |
| 2007/0244563 A1 | 10/2007 | Roche |
| 2008/0288079 A1 | 11/2008 | Leibel |
| 2009/0125113 A1 | 5/2009 | Guederian |
| 2010/0087876 A1 | 4/2010 | Gunther |
| 2010/0087877 A1 | 4/2010 | Gunther |
| 2010/0268239 A1 | 10/2010 | Sikora |
| 2011/0060417 A1 | 3/2011 | Simmen |
| 2011/0112648 A1 | 5/2011 | Gunther |
| 2013/0166033 A1 | 6/2013 | Gunther |
| 2014/0012388 A1 | 1/2014 | Brownhill et al. |
| 2015/0250601 A1 | 9/2015 | Humphrey |
| 2016/0095708 A1 | 4/2016 | Chavarria |
| 2016/0367375 A1 * | 12/2016 | Boulris ................. A61F 2/4081 |
| 2017/0273801 A1 | 9/2017 | Hodorek |
| 2018/0092760 A1 | 4/2018 | Sperling et al. |
| 2018/0214276 A1 | 8/2018 | Humphrey |
| 2018/0280151 A1 | 10/2018 | Humphrey |
| 2018/0303619 A1 * | 10/2018 | Kehres ...................... A61F 2/30 |

\* cited by examiner

IMPLANTS, SYSTEMS AND METHODS OF USING THE SAME

CROSS-REFERENCE TO RELATED APPLICATION

This application is a continuation of PCT/US2019/043986 filed Jul. 29, 2019 and entitled Implants, Systems and Methods of Using Same, which claims priority benefit under 35 U.S.C. § 119(e) of U.S. provisional application No. 62/711,425 filed Jul. 27, 2018 entitled Glenoid Implant, which are incorporated herein by reference in their entireties.

FIELD OF THE INVENTION

The present invention relates generally to general surgery, orthopedic implants used for replacing an articulation surface in a joint, such as shoulder prostheses. More specifically, but not exclusively, the present invention relates to the glenoid implants for anatomic shoulder arthroplasties, as well as methods for using the same.

BACKGROUND OF THE INVENTION

A natural shoulder joint may undergo degenerative changes due to a variety of causes. Accordingly, it is often necessary to replace a natural shoulder joint with a prosthetic shoulder joint. When implantation of such a shoulder joint prosthesis becomes necessary, the natural head portion of the humerus may be resected and a cavity may be created in the intramedullary canal of the host humerus for accepting a humeral component. The humeral component may include a head portion used to replace the natural head of the humerus. Once the humeral component has been implanted, the glenoid cavity positioned at the glenoid may also be resurfaced and shaped to accept a glenoid component. The glenoid component generally includes an articulating surface which is engaged by the head portion of the humeral component. Such an implant configuration is generally referred to as a traditional shoulder configuration.

In some instances, it may be necessary to convert the traditional shoulder configuration into a reverse shoulder configuration such as to achieve a higher level of constraint. In this regard, the humeral component and glenoid component may need to be removed and replaced with reverse shoulder components. When converting a traditional shoulder configuration to a reverse shoulder configuration, it is desirable to provide an efficient and minimally invasive transition on both the humeral side of the system and the glenoid side of the system. Exemplary shoulder implants are disclosed as follows:

U.S. Pat. No. 8,449,617 discloses a shoulder implant having a frame member, a cup, and a glenosphere. The frame member can have a central hub and a first arm extending therefrom. The frame member can be configured to selectively and alternatively couple with first shoulder implant components in a traditional shoulder configuration and with second shoulder implant components in a reverse shoulder configuration. The cup can have a concave surface that is configured to articulate with a humeral head component. The cup can be selectively coupled to the frame member in the traditional shoulder configuration. The glenosphere can have an outer articulating surface that is configured to articulate with a second cup. The glenosphere can be selectively coupled to the frame member in the reverse shoulder configuration.

U.S. Pat. No. 8,721,726 discloses a cup intended to interact with a prosthetic humeral head having a generally circular shape and positioning and anchoring devices for embedding the cup in an anatomical glenoid cavity in such a way that a load-bearing and sliding surface of the cup is integrated into the continuity of the anatomical cavity so as to be congruent with the humeral head.

U.S. Pat. No. 9,066,806 discloses a glenosphere configured to be mountable to a base plate. The glenosphere can be adapted to operate with a complementary humeral component. The base plate can include a removable taper member on a side of the base plate facing the glenosphere. The taper member can be configured to mount the glenosphere to the base plate.

U.S. Pat. No. 9,545,311 discloses a prosthesis that mechanically couples with both cancellous bone and cortical bone of a glenoid includes a head portion comprising a rear surface and an articular surface, an anchor member, and a plurality of deformable fins extending radially outward from the anchor member. The anchor member includes a distal end and a proximal end connected to the rear surface of the head portion. The plurality of deformable fins extend radially outward from the anchor member and includes at least a first proximal fin adjacent to the rear surface of the head portion positioned to engage with the cortical bone. The anchor member may also include at least one distal fin located proximate the distal end of the anchor member positioned to engage with the cancellous bone.

U.S. Pat. No. 9,844,440 discloses a glenoid implant including a body portion and a stem portion. The stem portion may extend from the body portion along a longitudinal axis. The body portion may include an articular side and a bone-engaging side opposite the articular side. At least a portion of the bone-engaging side may be disposed at a non-parallel angle relative to at least a peripheral edge of the articulation side.

U.S. Pat. No. 9,974,658 discloses a glenoid implant that has a protruding surface on a first side arranged to engage the surface of a cavity formed in a glenoid extending between peripheral glenoid surfaces and a flat surface adjacent the protruding surface of the implant arranged to engage the peripheral glenoid surfaces adjacent the cavity. The implant also has a wear-resistant surface on a second side opposite the flat surface and the protruding surface.

What is needed in the art is an anatomic shoulder glenoid implant having improved initial and long-term fixation while requiring minimal trauma to a patient's bone during implantation.

SUMMARY OF THE INVENTION

Aspects of the present invention provide glenoid implants for anatomic shoulder arthroplasties. The present invention also provides for methods for using the glenoid implants.

In one aspect, provided herein is an implant that includes a first portion, a second portion extending away from a bottom surface of the first portion, and a third portion extending away from the bottom surface of the first portion, wherein the third portion extends through the second portion.

In another aspect, provided herein is an orthopedic glenoid implant, the implant including a head, the head including a bone contacting surface and an opposing articular surface; a circular ring having a hollow interior and an inner diameter, the ring extending from the bone contacting surface in a direction opposite the articular surface, the ring having a central axis and a depth; a post, the post extending from the bone contacting surface in a direction opposite the articular surface, the post having an exterior diameter and a length, the length of the post greater than the depth of the ring, the exterior diameter of the post smaller than the inner diameter of the ring, the post disposed within the ring; at least one cortical bone engaging fin, the at least one cortical bone engaging fin disposed around and extending radially from the ring; at least one cancellous bone engaging fin, the at least one cancellous bone engaging fin disposed around and extending radially from the post, wherein each cancellous bone engaging fin is farther from the bone engaging surface than each cortical bone engaging fin.

In yet another aspect, provided herein are surgical methods for inserting the implant systems.

These, and other objects, features and advantages of this invention will become apparent from the following detailed description of the various aspects of the invention taken in conjunction with the accompanying drawings.

BRIEF DESCRIPTION OF DRAWINGS

The accompanying drawings, which are incorporated in and constitute a part of the specification, illustrate embodiments of the invention and together with the detailed description herein, serve to explain the principles of the invention. The drawings are only for purposes of illustrating preferred embodiments and are not to be construed as limiting the invention. It is emphasized that, in accordance with the standard practice in the industry, various features are not drawn to scale. In fact, the dimensions of the various features may be arbitrarily increased or reduced for clarity of discussion. The foregoing and other objects, features and advantages of the invention are apparent from the following detailed description taken in conjunction with the accompanying drawings in which.

DETAILED DESCRIPTION FOR CARRYING OUT THE INVENTION

Generally stated, disclosed herein are glenoid implants for shoulder prostheses. Further, surgical methods for using the glenoid implants are discussed.

In this detailed description and the following claims, the words proximal, distal, anterior, posterior, medial, lateral, superior and inferior are defined by their standard usage for indicating a particular part of a bone or implant according to the relative disposition of the natural bone or directional terms of reference. For example, "proximal" means the portion of a device or implant nearest the torso, while "distal" indicates the portion of the device or implant farthest from the torso. As for directional terms, "anterior" is a direction towards the front side of the body, "posterior" means a direction towards the back side of the body, "medial" means towards the midline of the body, "lateral" is a direction towards the sides or away from the midline of the body, "superior" means a direction above and "inferior" means a direction below another object or structure.

As used herein, the word "exemplary" or "illustrative" means "serving as an example, instance, or illustration." Any implementation described herein as "exemplary" or "illustrative" is not necessarily to be construed as preferred or advantageous over other implementations. Moreover, in the present description, the terms "upper", "lower", "left", "rear", "right", "front", "vertical", "horizontal", and derivatives thereof shall relate to the invention as oriented in the first figure of each embodiment.

Similarly, positions or directions may be used herein with reference to anatomical structures or surfaces. For example, as the current implants, devices, systems and methods are described herein with reference to use with the bones of the shoulder, the bones of the shoulder and upper arm may be used to describe the surfaces, positions, directions or orientations of the implants, devices, systems and methods. Further, the implants, devices, systems and methods, and the aspects, components, features and the like thereof, disclosed herein are described with respect to one side of the body for brevity purposes. However, as the human body is relatively symmetrical or mirrored about a line of symmetry (midline), it is hereby expressly contemplated that the implants, devices, systems and methods, and the aspects, components, features and the like thereof, described and/or illustrated herein may be changed, varied, modified, reconfigured or otherwise altered for use or association with another side of the body for a same or similar purpose without departing from the spirit and scope of the invention. For example, the implants, devices, systems and methods, and the aspects, components, features and the like thereof, described herein with respect to the right shoulder may be mirrored so that they likewise function with the left shoulder and vice versa. Further, the implants, devices, systems and methods, and the aspects, components, features and the like thereof, disclosed herein are described with respect to the shoulder for brevity purposes, but it should be understood that the implants, devices, systems and methods may be used with other bones of the body having similar structures, for example the lower extremity, and more specifically, with the bones of the ankle, foot, and leg.

Referring to the drawings, wherein like reference numerals are used to indicate like or analogous components throughout the several views, and with particular reference to FIGS. 1-6, there is illustrated an embodiment of a glenoid implant 100. The glenoid implant 100 includes a first end or medial end 102 and a second end or lateral end 104. The first end 102 is positioned opposite the second end 104. The glenoid implant 100 also includes a first portion or lateral portion 110, a second portion or intermediate portion 130, and third portion or medial portion 150. The first portion 110 may extend from the first end 102 toward the second end 104. The second portion 130 may extend away from a bottom surface of the first portion 110 toward the second end 104. The third portion 150 may also extend away from the bottom surface of the first portion 110 to the second end 104. The third portion 150 may extend through a central opening of the second portion 130.

Figure 1:
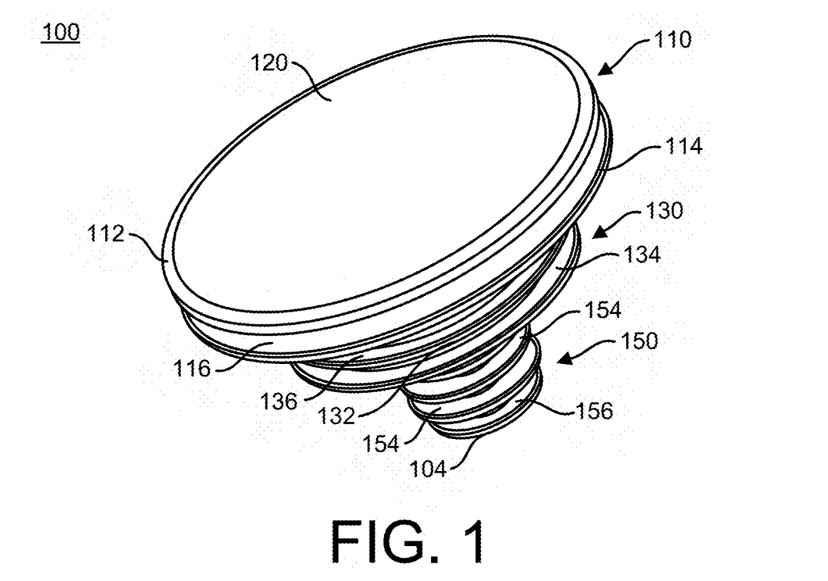
FIG. 1 is a first perspective view of an embodiment of a glenoid implant, in accordance with an aspect of the present disclosure.
Figure 2:
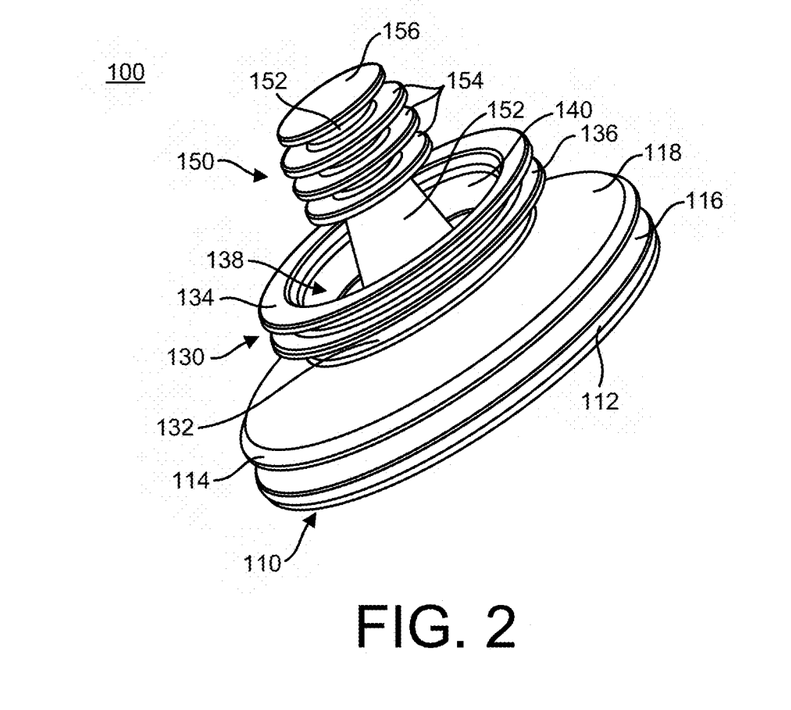
FIG. 2 is a second perspective view of the glenoid implant of FIG. 1, in accordance with an aspect of the present disclosure.
Figure 3:
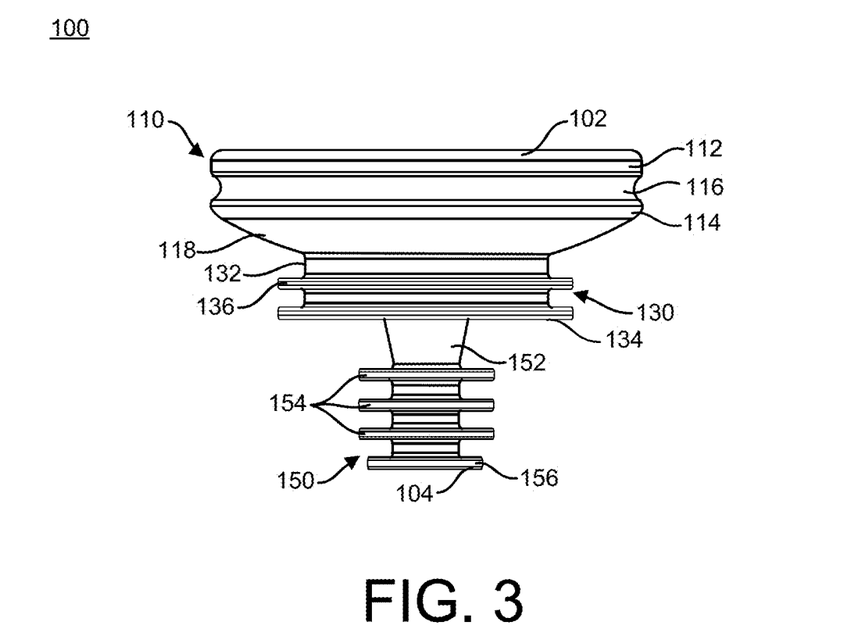
FIG. 3 is a side view of the glenoid implant of FIG. 1, in accordance with an aspect of the present disclosure.
Figure 4:
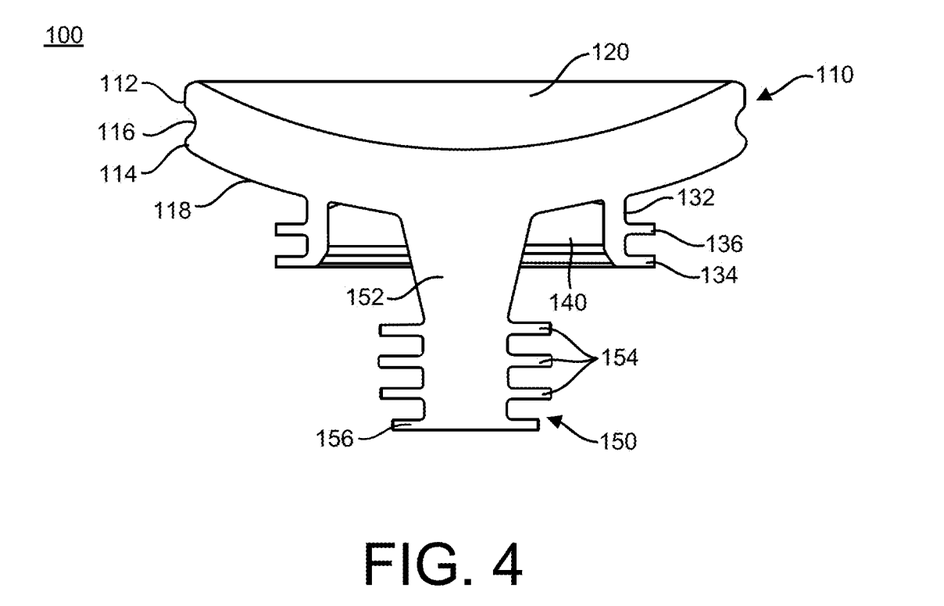
FIG. 4 is a cross-sectional view of the glenoid implant of FIG. 1 taken along line 4-4 in FIG. 5, in accordance with an aspect of the present disclosure.
Figure 5:
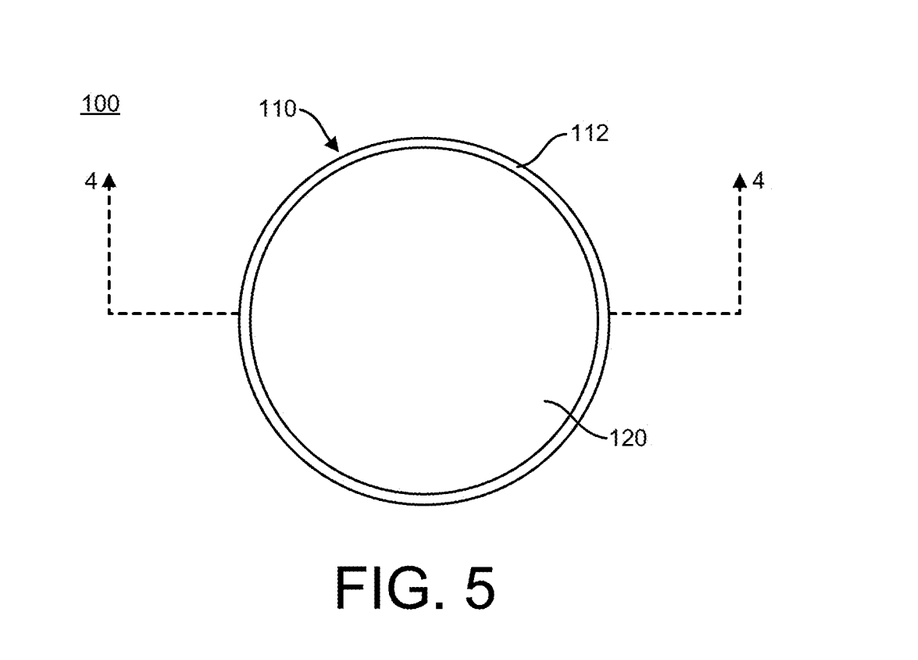
FIG. 5 is a top view of the stemless humeral implant of FIG. 1, in accordance with an aspect of the present disclosure.
Figure 6:
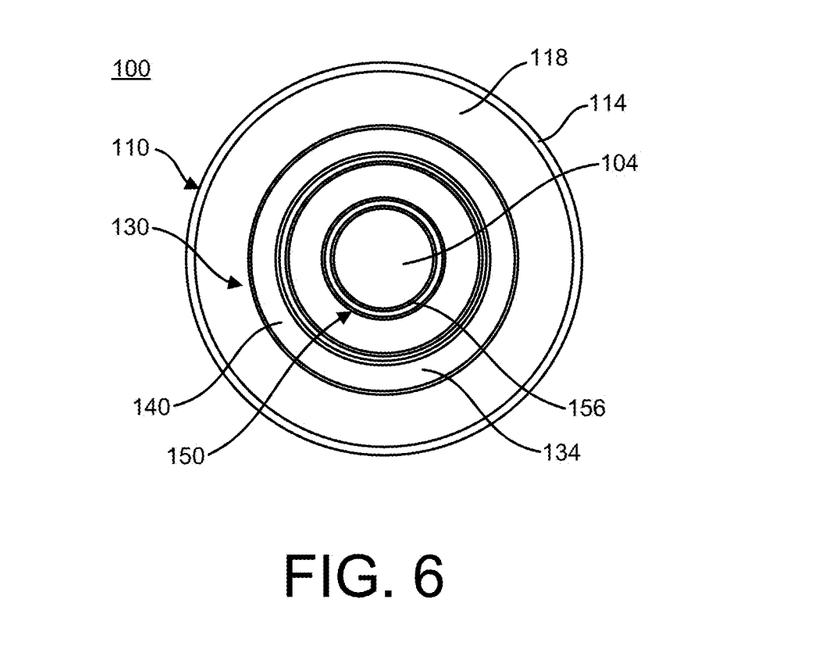
FIG. 6 is a bottom view of the stemless humeral implant of FIG. 1, in accordance with an aspect of the present disclosure.

With continued reference to FIGS. 1-6, the first portion 110 may include an exterior surface 112, 114, 116, 118 and an interior surface, articulating surface, or concave surface 120. The articulating surface 120 may be positioned on the first end 102 of the glenoid implant 100 and may be, for example, curved or arced into the first portion 110. More specifically, the articulating surface 120 may have, for example, a cone or spherical articular surface. Further, the articulating surface 120 may have, for example, a hybrid coned and spherical articular surface, as shown in FIG. 4, enabling conformity with any size humeral head to prevent sliding of the head superiorly. The exterior surface 112, 114, 116, 118 may include a first rim or distal rim 112, a second rim or proximal rim 114, a groove or circumferential channel 116, and a tapered region or bone contacting surface 118. The first rim 112 may extend circumferentially around the first portion 110. The second rim 114 may also extend circumferentially around the first portion 110 and may be spaced apart from the first rim 112. The groove 116 may be positioned between the first rim 112 and the second rim 114. The groove 116 may also be inset into the exterior surface of the first portion 110. The tapered region 118 may extend from the second rim 114 to the second portion 130. The tapered region 118 may also be, for example, angled, curved, or arced as it extends between the second rim 114 and the second portion 130.

As shown in FIGS. 1-6, the second portion 130 may include a base member or extension member 132 extending away from the tapered region 118 toward the second end 104 of the glenoid implant 100. The base member 132 may be, for example, a constant or continuous ring extending circumferentially around the bottom of the tapered region 118 of the first portion 110. Although not shown, it is also contemplated that the base member 132 may be non-continuous or include gaps, spaces or the like interruptions around the circumference of the base member 132. The base member 132 may be, for example, configured or sized and shaped to provide improved fixation and support to the glenoid implant 100. The second portion 130 may also include a first lip 134 and a second lip 136 extending circumferentially around the exterior surface of the second portion 130. As shown the base member include two lips 134, 136, however, alternative numbers of lips 134, 136 are also contemplated and may range from, for example, one lip to five lips. The lips 134, 136 may extend away from the base member 132, for example, in a range of approximately 12 mm to approximately 31 mm. In addition, the second portion 130 may include a recessed region or opening 138 extending through the second portion 130 and forming an interior surface 140 of the base member 132. The interior surface 140 is positioned opposite the first lip 134 and the second lip 136 on the base member 132. The first and second lips 134, 136 may be, for example, locking fins designed for cortical fixation.

Referring now to FIGS. 1-4 and 6, the third portion or medial portion 150 may include a stem 152, at least one protrusion 154, and a medial end member 156. The stem or central post 152 may extend away from the bottom of the bone contacting surface 118 of the first portion 110 through the base member 132. The stem 152 may, for example, have a uniform diameter along its entire length, be tapered along its entire length, or have a combination of portions with a uniform diameter and portions tapered along their length. For example, as shown in FIGS. 2-4, the stem 152 may be tapered as it extends towards the second end 104 from the bottom of the bone contacting surface 118 to a first protrusion 154, thereafter, the stem 152 may have a uniform diameter until engages the medial end member 156. The at least one protrusion or locking fin 154 may extend away from the stem 152, for example, circumferentially forming a constant or continuous member. As shown the at least one protrusion 154 may be, for example, three protrusions. Alternative numbers of protrusions are also contemplated and may range from, for example, two protrusions to eight protrusions. The medial end member or locking fin 156 may have, for example, a disk-like or coin-like shape coupled to the end of stem 152. The medial end member 156 may have a first diameter, the end of the stem 152 positioned at the second end 104 of the glenoid implant 100 may have a second diameter, and the first diameter may be larger than the second diameter. In addition, the at least one protrusion 154 may have third diameter and the third diameter may be larger than both the first diameter and the second diameter. The at least one protrusion 154 and the medial end member 156 form locking fins surrounding the stem 152 which may be, for example, configured or sized and shaped for cancellous fixation.

Figure 7:
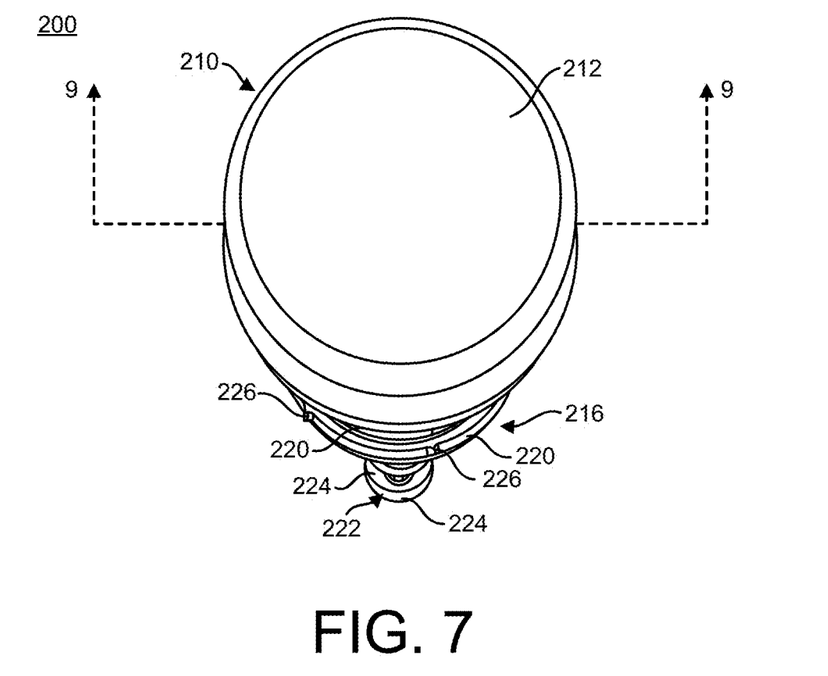
FIG. 7 is an isometric view of another glenoid implant, in accordance with an aspect of the present disclosure.
Figure 8:
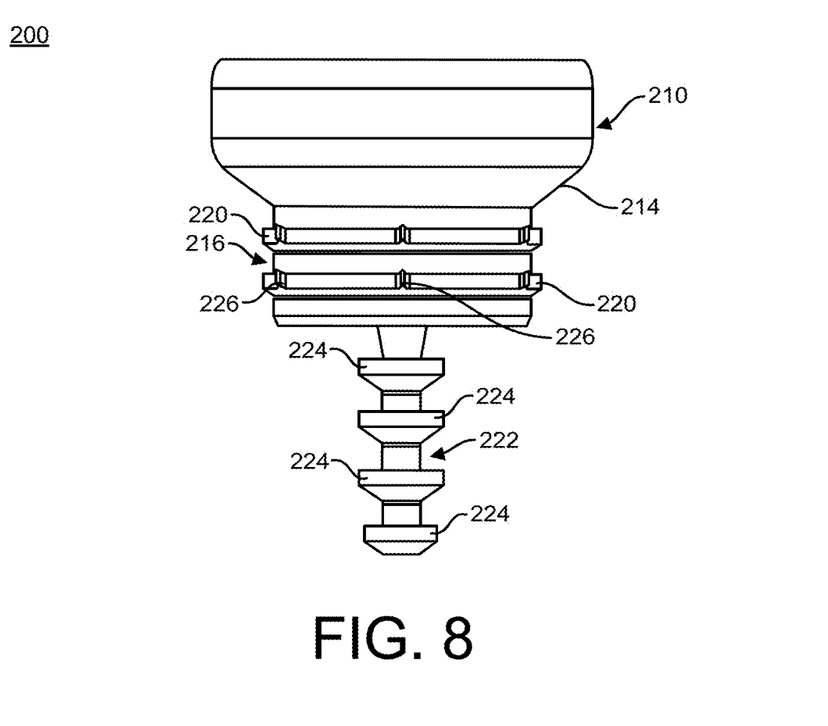
FIG. 8 is a side view of the glenoid implant of FIG. 7, in accordance with an aspect of the present disclosure.
Figure 9:
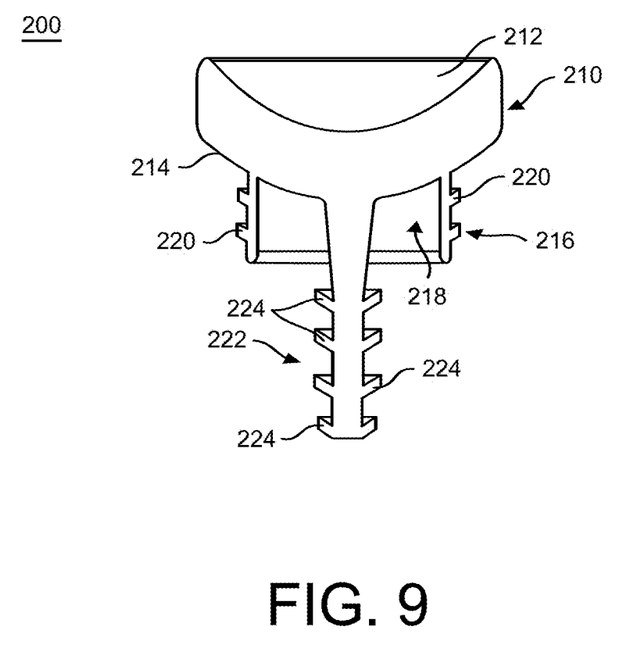
FIG. 9 is a side cross-sectional view of the glenoid implant of FIG. 7, in accordance with an aspect of the present disclosure.
Figure 10:
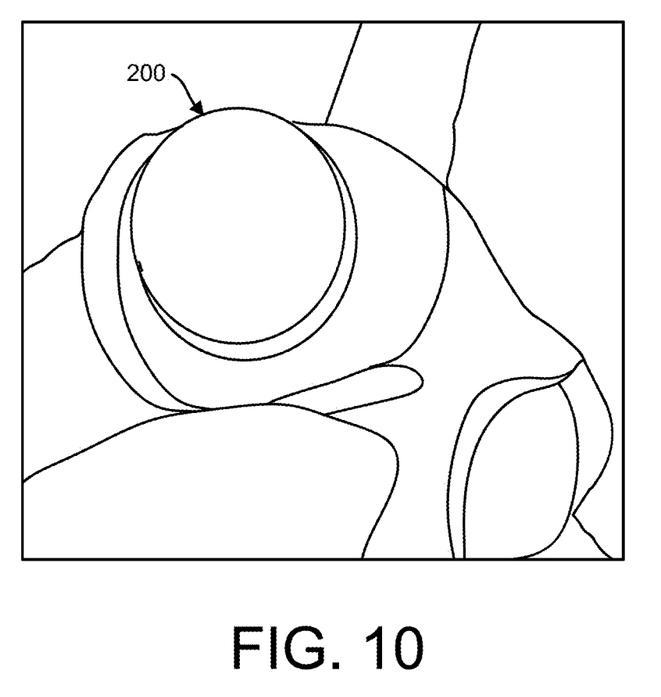
FIG. 10 is an isometric view of the glenoid implant of FIG. 7 implanted into a bone, in accordance with an aspect of the present disclosure.

Referring now to FIGS. 7-12, an isometric view of a glenoid implant 200 is shown. As shown in FIG. 7, the implant 200 includes a generally cylindrically shaped head 210 with a concave articular surface 212 and an opposite preferably convex bone contacting surface 214. FIG. 10 shows the implant 200 implanted into a bone.

Figure 11:
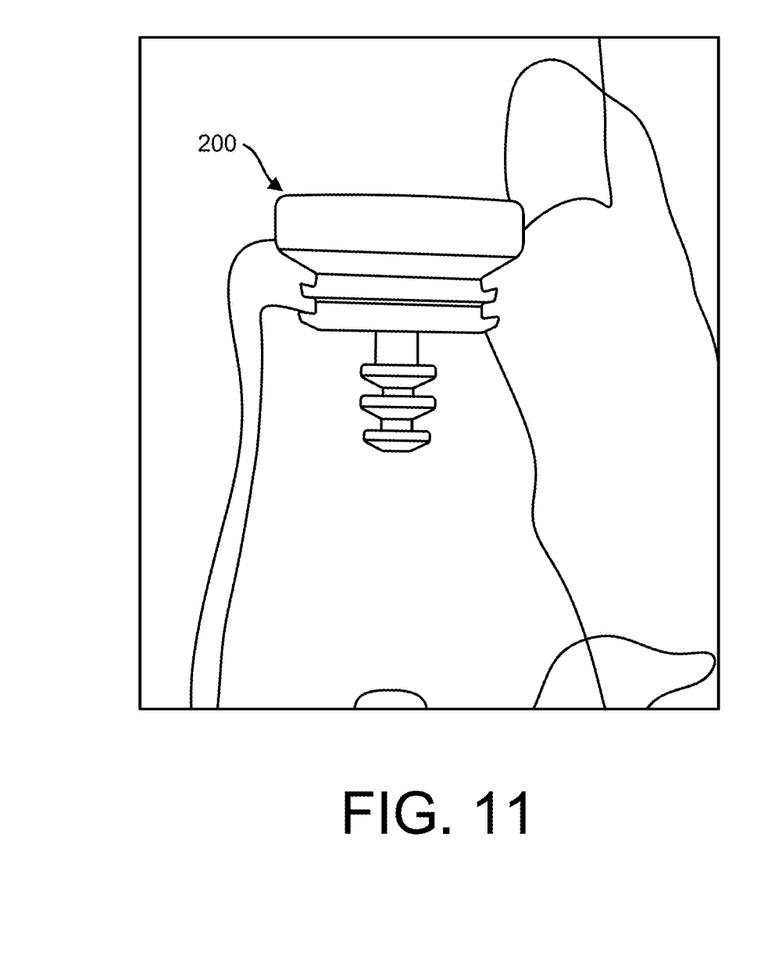
FIG. 11 is a side view of the glenoid implant of FIG. 7 implanted into a bone, in accordance with the present disclosure.
Figure 12:
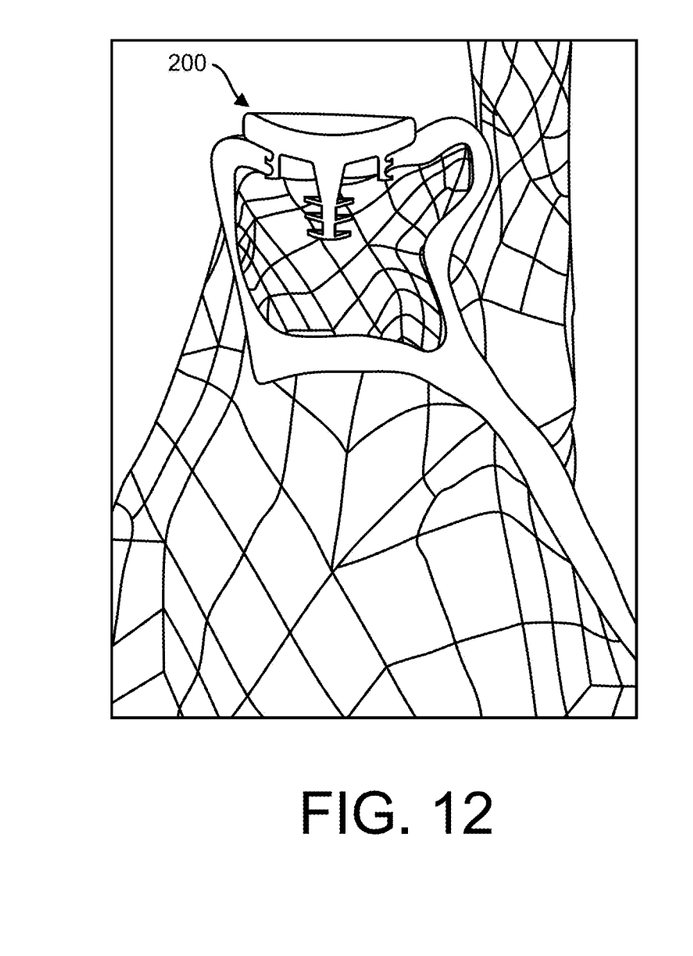
FIG. 12 is a side cross-sectional view of the glenoid implant of FIG. 7 implanted into a bone, in accordance with an aspect of the present disclosure.

With continued reference to FIGS. 9 and 12, the implant 200 also includes a circular ring 216 with a hollow interior 218 and an inner diameter. The ring 216 extends from the bone contacting surface 214 in a direction opposite the articular surface 212. The ring 216 has a central axis and a depth. Although not shown, it is also contemplated that the ring 216 may be non-continuous or include gaps, spaces, or like interruptions around the circumference of the ring 216. The implant 200 further includes at least one cortical bone engaging fin 220 disposed around and extending radially from the ring 216. Preferably, at least two (2) fins 220 extend from the ring 216. The fins 220 may include, for example, a plurality of teeth or protrusions 226 spaced circumferentially around the exterior surface of the fins 220. The fins 220 may, for example, partially flex when the ring 216 is inserted into cortical bone, such as illustrated in FIGS. 10-12. The fins 220 may extend, for example, from the ring 216 at an obtuse or acute angle. Alternatively, the fins 220 may extend from the ring 216 horizontally, i.e. at a 90-degree angle. It is also contemplated that the fins 220 may be, for example, non-continuous or include gaps, spaces, or interruptions as the fins 220 extend around the circumference of the ring 216.

Referring again to FIGS. 8 and 9, the implant 200 also includes a post or stem 222 extending from the bone contacting surface 214 in a direction opposite articular surface 212. The post 222 has an exterior diameter and a length. The length of the post 222 is greater than the depth of the ring 216. The exterior diameter of the post 222 is less than the inner diameter of the ring 216. The post 222 is disposed within the ring 216 such that the post 222 and the ring 216 share a common central axis.

With continued reference to FIGS. 8 and 9, the implant 200 also includes at least one cancellous bone engaging fin 224 disposed around and extending radially from the post 222. The at least one cancellous bone engaging fin 224 may be, for example, at least two (2) fins 224 extending from the post 222. The fins 224 partially flex when the post 222 is inserted into cancellous bone as illustrated in FIGS. 10-12. The fins 224 preferably extend from the post 222 at an angle, for example, an obtuse or acute angle. However, the fins 224 may also extend from the post 222 horizontally, i.e. at a 90-degree angle. Each cancellous bone engaging fin 224 is farther from the bone engaging surface 214 than each cortical bone engaging fin 220.

Advantageously, the implant 200 discretely engages and locks into cancellous bone and separately into cortical bone. The bone may be prepared to receive the implant 200 by a reaming operation. Moreover, the ring 216 of implant 200 can also be adapted to a reverse baseplate.

The wider, shallower ring 216 designed for cortical engagement provides for fixation farther toward the edge of the implant 200 and reduces the chance of implant movement. Glenoid implants may be subjected to what is called "rocking horse" where the edges lift up when the humeral head puts pressure on the opposite side of the implant. Fixation out towards the edge is ideal to prevent this from happening. Other devices include pegs on the outer periphery to achieve stabilization, but glenoid rigidity could b e compromised from a large quantity of holes; so, there is limited ability to prevent rocking horse.

In addition, the wider, shallower ring 216 on the outside and the longer, thinner post 222 on the inside are more conducive to the shape of the glenoid vault. The glenoid is widest at the articular surface and necks down rapidly. Perforation through the far cortex with a reaming or drilling operation is not ideal as cement can leak out those perforations and into the joint space and can be undetected. Devices with multiple peripheral pegs that are long enough can achieve stabilization, but they can perforate. Thus, the constant shallow ring 216 of implant 200 provides for better stabilization without such perforation.

Figure 13:
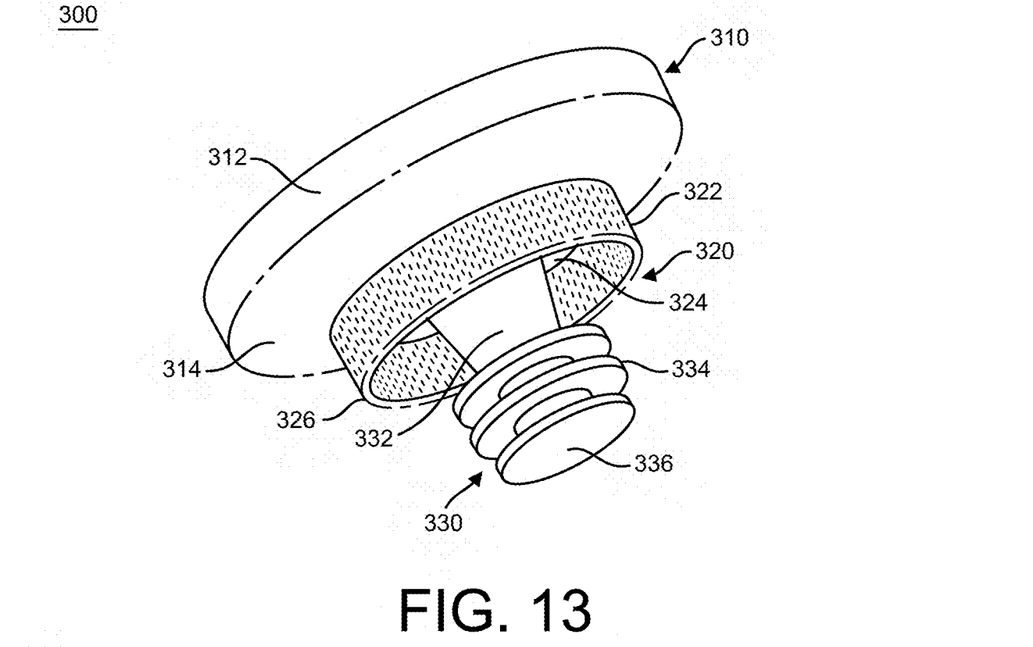
FIG. 13 is a perspective view of another glenoid implant, in accordance with an aspect of the present disclosure.
Figure 14:
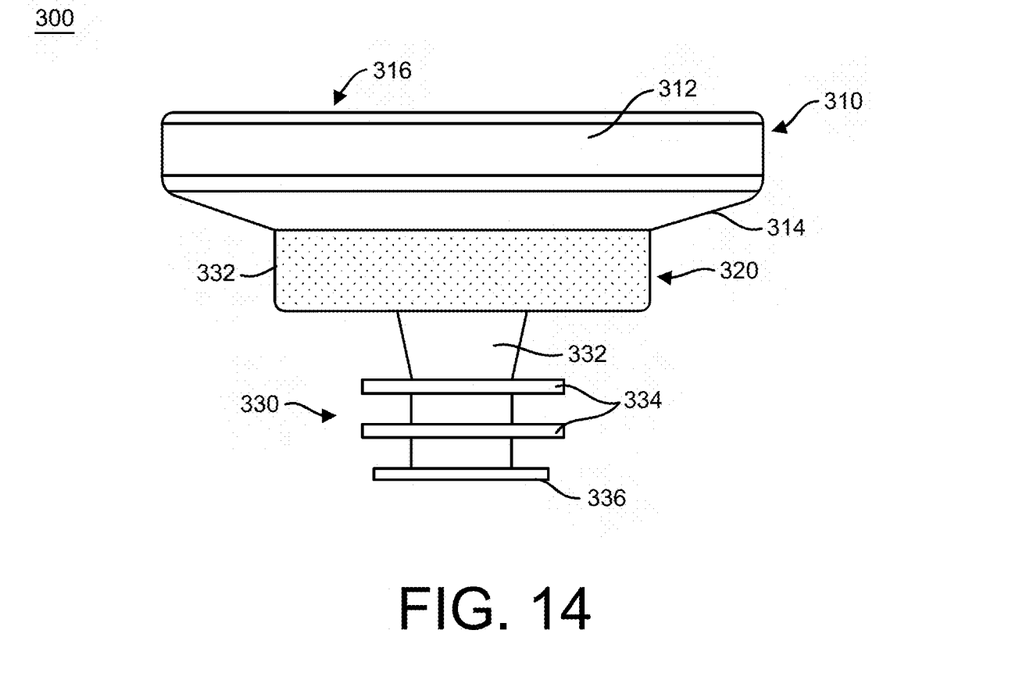
FIG. 14 is a side view of the glenoid implant of FIG. 13, in accordance with an aspect of the present disclosure.
Figure 15:
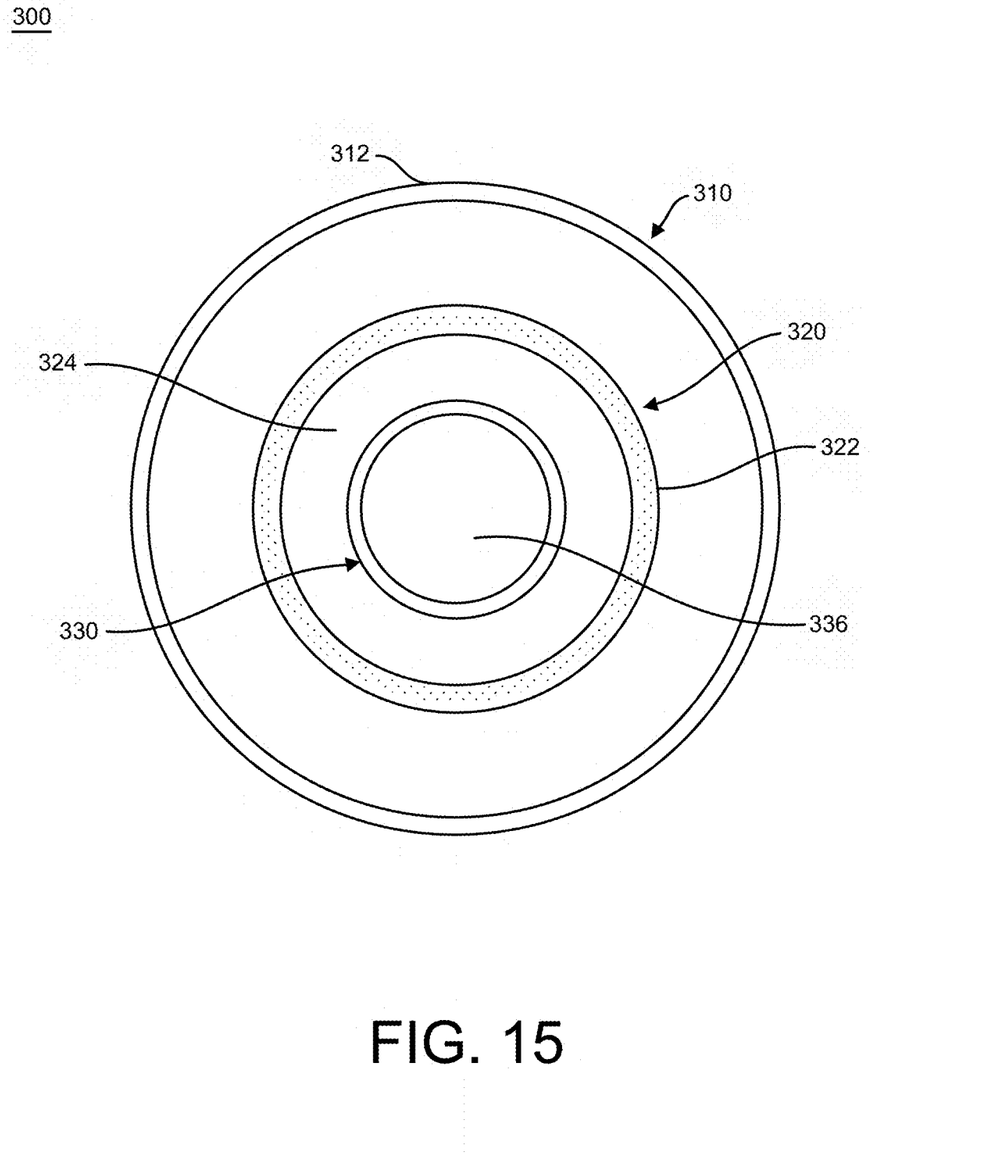
FIG. 15 is a bottom view of the glenoid implant of FIG. 13, in accordance with an aspect of the present disclosure.

Referring now to FIGS. 13-15, another glenoid implant 300 is shown. The glenoid implant 300 may include a first end 302 and a second end 304. The glenoid implant 300 may also include a first portion or lateral portion 310, a second portion or intermediate portion 320, and third portion or medial portion 330. The first portion 310 may extend from the first end 302 toward the second end 304 the second portion 320 may extend away from a bottom surface of the first portion 310 toward the second end 304. The third portion 330 may extend through a central opening of the second portion 320. The implant 300 may have, for example, a porous metal ring or third portion 330 and a porous metal post or stem (not shown) with a compression molded poly articular surface 316. The porous metal post or stem (not shown) may be, for example, tapered as it extends away from the bottom surface of the lateral portion 310.

With continued reference to FIGS. 13-15, the first portion 310 may include a rim or exterior surface 312, a tapered region or bone contacting surface 314, and an arced to articulating surface, concave surface or anterior surface 316. The exterior surface 312 may be, for example, generally flat or planar as that extends between the first end 102 and the bone contacting surface 314. As shown in FIG. 15, the exterior surface 312 may have, for example, a cylindrical shape.

The articulating surface 316 may be positioned on the first end 302 of the glenoid implant 300 and may be, for example, curved or arced into the first portion 310. More specifically, the articulating surface 316 may have, for example, a cone or spherical articular surface. Further, the articulating surface 316 may have, for example, a hybrid coned and spherical articular surface (not shown) enabling head to prevent sliding of the head superiorly. The bone contacting surface 314 may extend from the bottom of the rim 312 to the second portion 320. The bone contacting surface 314 may be, for example, angled, curved, or arced as they extend between the bottom of the rim 312 and the second portion 320.

As shown in FIGS. 13-15, the second portion 320 may extend away from the tapered region 314 toward the second end 304 of the glenoid implant 100. The second portion 320 may be, for example, a constant or continuous ring extending circumferentially around the bottom of the tapered region 314 of the first portion 310. The second portion 320 may be, for example, straight or tapered as it extends from the bone contacting surface 314. Although not shown, it is also contemplated that the second portion 320 may be non-continuous or include gaps, spaces or the like interruptions around the circumference of the second portion 320. The second portion 320 may be, for example, configured or sized and shaped to provide improved fixation and support to the glenoid implant 300. The second portion 320 may have, for example, a textured surface or textured coating 322. The textured surface 322 may, for example, assist with cortical fixation. In addition, the second portion 320 may include a recessed region or opening 324 extending through the second portion 320 and forming an interior surface 326 of the second portion 320. The interior surface 326 is positioned opposite an exterior surface.

Referring now to FIGS. 13 and 14, the third portion or medial portion 330 may include a stem 332, at least one protrusion 334, and a medial end member 336. The stem or central post 332 may extend away from the bottom of the bone contacting surface 314 of the first portion 310 through the second portion 320 the stem 332 may, for example, have a uniform diameter along its entire length, be tapered along its entire length, or have a combination of portions with a uniform diameter and portions which are tapered along their length. For example, as shown in FIGS. 13 and 14, the stem 332 may be tapered as the stem 332 extends towards the second end 304 from the bottom of the bone contacting surface 314 to a first protrusion 334, thereafter, the stem may have a uniform diameter until the stem 332 engages the medial end member 336. The at least one protrusion or locking fin 334 may extend away from the stem 332, for example, circumferentially forming a constant or continuous member. As shown, the at least one protrusion 334 may be, for example, to protrusions 334. Alternative numbers of protrusions 334 are also contemplated and may range from, for example, two protrusions to eight protrusions. The medial end member or locking fin 336 may have, for example, a disk-like or coin-like shape coupled to the end of stem 332. The medial end member 336 may have a first diameter, the end of the stem 332 positioned at the second end 304 of the glenoid implant 300 may have a second diameter, and the first diameter may be larger than the second diameter. In addition, the at least one protrusion 334 may have third diameter and the third diameter may be larger than both the first diameter and the second diameter. The at least one protrusion 334 and the medial end member 336 and locking fence surrounding the stem 332 which may be, for example, configured or sized and shaped for cancellous fixation.

A surgical method for implanting the glenoid implants 100, 200, 300, may include preparing the patient's joint by performing sizing and alignment steps. Next, the bone may be reamed to form a channel and recess to receive the glenoid implant 100, 200, 300. Once the bones are prepared, implant trials may be used to determine the desired size of the glenoid implant 100, 200, 300 for implantation. Next the selected glenoid implant 100, 200, 300 may be inserted and coupled to the bones. Finally, the surgical procedure may be completed and the patient's incision may be closed.

As may be recognized by those of ordinary skill in the art based on the teachings herein, numerous changes and modifications may be made to the above-described and other embodiments of the present disclosure without departing from the scope of the disclosure. The components of the implants, devices, and/or systems as disclosed in the specification, including the accompanying abstract and drawings, may be replaced by alternative component(s) or feature(s), such as those disclosed in another embodiment, which serve the same, equivalent or similar purpose as known by those skilled in the art to achieve the same, equivalent or similar results by such alternative component(s) or feature(s) to provide a similar function for the intended purpose. In addition, the implants, devices, and/or systems may include more or fewer components or features than the embodiments as described and illustrated herein. For example, the components and features of implants 100, 200, 300 may be used interchangeably and in alternative combinations as would be modified or altered by one of skill in the art. Further, the steps of the surgical methods associated with the implants 100, 200, 300 may be used interchangeably and in alternative combinations as would be modified or altered by one of skill in the art. Accordingly, this detailed description of the currently-preferred embodiments is to be taken in an illustrative, as opposed to limiting of the disclosure.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has", and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Furthermore, a device or structure that is configured in a certain way is configured in at least that way, but may also be configured in ways that are not listed.

The invention has been described with reference to the preferred embodiments. It will be understood that the operational embodiments described herein are exemplary of a plurality of possible arrangements to provide the same general features, characteristics, and general system operation. Modifications and alterations will occur to others upon a reading and understanding of the preceding detailed description. It is intended that the invention be construed as including all such modifications and alterations.

Having thus described the preferred embodiments, the invention is now claimed to be:

1. An implant, comprising:
    a first portion, wherein the first portion comprises:
        at least one rim positioned on an exterior surface of the first portion;
        an articulating surface recessed into a first end of the first portion; and
        a bone contacting surface on a second end of the first portion positioned opposite the articulating surface;
    a second portion extending away from a bottom surface of the first portion, wherein the second portion comprises:
        a base member extending away from the bone contacting surface of the first portion; and
        a recessed region extending into the base member from a second end of the base member to the bone contacting surface of the first portion; and
    a third portion extending away from the bottom surface of the first portion, wherein the third portion extends through the second portion and the recessed region is positioned between the base member and the third portion; and
    wherein an interior surface of the base member is spaced apart from an exterior surface of the third portion.

2. The implant of claim 1, wherein the at least one rim comprises:
    a first rim positioned at the first end of the first portion;
    a second rim positioned at the second end of the first portion and spaced apart from the first rim; and
    a groove circumferentially inset into the exterior surface of the first portion and positioned between the first rim and the second rim.

3. The implant of claim 1, wherein the at least one rim is one rim having a planar surface.

4. The implant of claim 1, wherein the articulating surface is at least one of cone-shaped and spherical shaped.

5. The implant of claim 1, wherein the articulating surface is a hybrid coned and spherical shape.

6. The implant of claim 1, wherein the bone contacting surface is tapered between the at least one rim and the second portion.

7. The implant of claim 1, wherein the base member further comprises:
    at least one lip extending away from an exterior surface of the base member.

8. The implant of claim 7, wherein the at least one lip comprises:
    a first lip; and
    a second lip positioned at the second end of the base member;
    wherein the first lip is positioned between the second lip and the bone contacting surface of the first portion.

9. The implant of claim 1, wherein the base member has a textured surface.

10. The implant of claim 1, wherein at least one of a first lip and a second lip comprise a plurality of teeth extending away from the at least one of the first lip and the second lip.

11. The implant of claim 1, wherein third portion comprises:
a stem coupled to and extending away from the bone contacting surface of the first portion, wherein the stem extends through an opening formed by the recessed region in the base member of the second portion.

12. The implant of claim 11, wherein the third portion further comprises:
at least one protrusion coupled to and extending away from an exterior surface of the stem; and
a medial end member coupled to a second end of the stem.

13. The implant of claim 12, wherein the at least one protrusion is two protrusions spaced apart between the second end of the base member and the medial end member.

14. The implant of claim 12, wherein the at least one protrusion is three protrusions spaced apart between the second end of the base member and the medial end member.

15. The implant of claim 12, wherein the stem comprises:
a first portion extending from the bone contacting surface of the first portion to a first protrusion of the at least one protrusion; and
a second portion extending from the first protrusion two the second end of the third portion;
wherein the first portion is tapered.

16. The implant of claim 12, wherein the at least one protrusion has a first diameter and the medial end member is a second diameter, and wherein the first diameter is larger than the second diameter.

17. The implant of claim 1, wherein the base member is non-continuous.

18. An orthopedic glenoid implant, the implant comprising:
a head comprising:
a bone contacting surface; and
an opposing articular surface;
a circular ring having a hollow interior and an inner diameter, the ring extending from the bone contacting surface in a direction opposite the articular surface, the ring having a central axis and a depth, wherein the depth extends from the bone contacting surface parallel with the central axis;
a post extending from the bone contacting surface in a direction opposite the articular surface, the post having an exterior diameter and a length, the length of the post greater than the depth of the ring, the exterior diameter of the post smaller than the inner diameter of the ring forming the hollow interior between an interior surface of the circular ring and an exterior surface of the post, and the post disposed within the ring;
at least one cortical bone engaging fin disposed around and extending radially from the ring;
at least one cancellous bone engaging fin disposed around and extending radially from the post, wherein each cancellous bone engaging fin is farther from the bone contacting surface than each cortical bone engaging fin.

19. The implant of claim 18, wherein the bone contacting surface is curved.

20. The implant of claim 18, wherein the bone contacting surface is flat.

21. The implant of claim 18, wherein the at least one cortical bone engaging fin extends at a 90-degree angle from the ring.

22. The implant of claim 18, wherein the at least one cortical bone engaging fin extends at an acute angle from the ring.

23. The implant of claim 18, wherein the at least one cortical bone engaging fin extends at an obtuse angle from the ring.

24. The implant of claim 18, wherein the at least one cortical bone engaging fin is flexible.

25. The implant of claim 18, wherein the at least one cancellous bone engaging fin extends at a 90-degree angle from the post.

26. The implant of claim 18, wherein the at least one cancellous bone engaging fin extends at an acute angle from the post.

27. The implant of claim 18, wherein the at least one cancellous bone engaging fin extends at an obtuse angle from the post.

28. The implant of claim 18, wherein the at least one cancellous bone engaging fin is flexible.

29. The implant of claim 18, wherein the ring further comprises anti-rotation barbs extending away from the at least one cortical bone engaging fin.

30. An orthopedic glenoid implant, comprising:
a head comprising:
a bone contacting surface; and
an opposing articular surface;
a first anchor member extending from the bone contacting surface in a direction opposite the articular surface, the first anchor member having a depth and a hollow interior, wherein the depth is measured from a free end of the first anchor member to a portion of the first anchor member coupled to the bone contacting surface;
a second anchor member extending from the bone contacting surface in a direction opposite the articular surface, the second anchor member having a length, the length of the second anchor member being greater than the depth of the first anchor member, the second anchor member disposed within the first anchor member, and wherein a void is formed between an exterior surface of the second anchor member and an interior surface of the first anchor member;
at least one cortical bone engaging fin, the at least one cortical bone engaging fin disposed around and extending from the first anchor member;
at least one cancellous bone engaging fin, the at least one cancellous bone engaging fin disposed around and extending from the second anchor member, wherein each cancellous bone engaging fin is positioned farther from the bone contacting surface than each cortical bone engaging fin.

31. The implant of claim 30, wherein the bone contacting surface is curved.

32. The implant of claim 30, wherein the bone contacting surface is flat.

33. The implant of claim 30, wherein the at least one cortical bone engaging fin extends at a 90-degree angle from the first anchor member.

34. The implant of claim 30, wherein the at least one cortical bone engaging fin extends at an acute angle from the first anchor member.

35. The implant of claim 30, wherein the at least one cortical bone engaging fin extends at an obtuse angle from the first anchor member.

36. The implant of claim 30, wherein the at least one cortical bone engaging fin is flexible.

37. The implant of claim 30, wherein the at least one cancellous bone engaging fin extends at a 90-degree angle from the second anchor member.

38. The implant of claim 30, wherein the at least one cancellous bone engaging fin extends at an acute angle from the second anchor member.

39. The implant of claim 30, wherein the at least one cancellous bone engaging fin extends at an obtuse angle from the second anchor member.

40. The implant of claim 30, wherein the at least one cancellous bone engaging fin is flexible.

41. The implant of claim 30, wherein the first anchor member further comprises anti-rotation barbs extending away from the at least one cortical bone engaging fin.

42. The implant of claim 1, wherein an exterior surface of the base member has a diameter smaller than a diameter of the exterior surface of the first portion.

\* \* \* \* \*